United States Patent
Suehara (10) Patent No.: US 9,861,789 B2
(45) Date of Patent: Jan. 9, 2018

(54) ACTUATING MEMBER AND MEDICAL INSTRUMENT

(71) Applicant: Terumo Kabushiki Kaisha, Tokyo (JP)

(72) Inventor: Satoru Suehara, Kaisei-machi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 547 days.

(21) Appl. No.: 14/517,655

(22) Filed: Oct. 17, 2014

(65) Prior Publication Data
US 2015/0107396 A1 Apr. 23, 2015

(30) Foreign Application Priority Data
Oct. 18, 2013 (JP) ................................ 2013-217558

(51) Int. Cl.
*A61M 25/01* (2006.01)

(52) U.S. Cl.
CPC ..... *A61M 25/0147* (2013.01); *A61M 25/0136* (2013.01); *A61M 25/0138* (2013.01); *Y10T 74/20323* (2015.01)

(58) Field of Classification Search
CPC .......... A61M 25/0147; A61M 25/0136; A61M 25/0138; Y10T 74/20323
See application file for complete search history.

(56) References Cited

U.S. PATENT DOCUMENTS

| 5,358,478 A * | 10/1994 | Thompson | A61M 25/0136 |
| | | | 604/528 |
| 5,472,017 A * | 12/1995 | Kovalcheck | A61B 1/0052 |
| | | | 138/103 |
| 2008/0139886 A1 | 6/2008 | Tatsuyama | |

FOREIGN PATENT DOCUMENTS

JP 2008-142199 A 6/2008

OTHER PUBLICATIONS

Merriam-Webster Dictionary definition for operate, definition 2, available online Mar. 20, 2017 at https://www.merriam-webster.com/dictionary/operate.*

* cited by examiner

*Primary Examiner* — Kevin C Sirmons
*Assistant Examiner* — Amber Stiles
(74) *Attorney, Agent, or Firm* — Foley & Lardner LLP (57) ABSTRACT

An actuating member for causing a flexible elongated member for medical use to perform a predetermined curving motion includes a push-pull member including a first moving part and a second moving part which are configured to be movable relative to one another in an axial direction of the elongated member, the first moving part and the second moving part being pushable and pullable so as to cause the elongated member to curve in the axial direction of the elongated member; a curving motion restricting member which is configured to be movable in the axial direction of the elongated member, and which is configured to restrict curving of at least a portion of the elongated member; and an operation member configured to operate movements of the first moving part, the second moving part, and the curving motion restricting member.

20 Claims, 10 Drawing Sheets

ACTUATING MEMBER AND MEDICAL INSTRUMENT

CROSS-REFERENCE TO RELATED APPLICATION

This application claims priority to Japanese Patent Application No. 2013-217558, filed on Oct. 18, 2013, which is hereby incorporated by reference in its entirety.

BACKGROUND

The present disclosure relates to an actuating member for causing an elongated member for medical use to perform a predetermined curving motion, and a medical instrument including the actuating member.

In the medical field, flexible elongated members are generally used for administration of a drug into a living body, suction or injection of various fluids, introduction of a medical instrument into a living body, or other similar purposes. Such an elongated member is inserted into a lumen (e.g., a blood vessel or a body cavity) in a living body and is guided along a curved path, such as the lumen, to a target site such as a treatment site, or the vicinity thereof, in the living body. Therefore, the elongated member may be used in the state of having incorporated therein an actuating member for a curving operation that can be put into an arbitrary curving operation through an operator's hand operation (see, for example, Japanese Patent Laid-Open No. 2008-142199).

In Japanese Patent Laid-Open No. 2008-142199, an actuating member which includes an operation wire connected to an insertion part (elongated member) to be inserted into a living body, a pulley having the operation wire wound thereon, and a curving operation knob (operation member) for putting the pulley into rotation, and an endoscope in which the actuating member is incorporated are described. The actuating member curves the elongated member by pushing/pulling the operation wire through rotating the curving operation knob, which is disposed at a proximal side of the endoscope, about an axis orthogonal to an axial direction of the elongated member.

In the actuating member according to the related art such as the one described in Japanese Patent Laid-Open No. 2008-142199, however, the elongated member is curved with a radius of curvature being gradually decreased as the operation amount of the operation member increases. Therefore, it is impossible to curve the elongated member with a small radius of curvature at a stage where the operation amount is still small, or to curve the elongated member with a large radius of curvature at a stage where the operation amount has become large. Accordingly, the elongated member cannot be appropriately curved in conformity with a target site in a living body.

SUMMARY OF INVENTION

One objective of certain embodiments of the present invention is to provide an actuating member capable of causing an elongated member to curve appropriately according to a target site in a living body, and a medical instrument including the actuating member.

According to one embodiment of the present invention, there is provided an actuating member for causing a flexible elongated member for medical use to perform a predetermined curving motion, the actuating member including: a push-pull member having a first moving part and a second moving part which are provided to be relatively movable in an axial direction of the elongated member, the first moving part and the second moving part configured to be pushed and pulled so as to cause the elongated member to perform a curving motion in the axial direction of the elongated member; a curving motion restricting member which is provided to be movable in the axial direction of the elongated member and which is configured to restrict the curving motion of the elongated member; and an operation member which operates movements of the first moving part, the second moving part, and the curving motion restricting member, wherein one of the first moving part and the operation member is provided with a first guide groove for guiding a movement of the first moving part, one of the second moving part and the operation member is provided with a second guide groove for guiding a movement of the second moving part, and one of the curving motion restricting member and the operation member is provided with a third guide groove for guiding a movement of the curving motion restricting member.

In one aspect, it is possible to move the first moving part, the second moving part, and the curving motion restricting member by means of the guide grooves through operation of the operation member. This ensures that when the elongated member is curved through a relative movement of the first moving part and the second moving part, the curving motion of the elongated member can be restricted according to the moved position of the curving motion restricting member. Therefore, the elongated member can be put into a variety of curving motions, according to the settings of the guide grooves. Consequently, the elongated member can be appropriately curved in conformity with a target site in a living body.

In one aspect, the third guide groove includes a first region so configured that the curving motion restricting member is immovable, and a second region so configured that the curving motion restricting member is movable.

This configuration ensures that whether or not the curving motion restricting member is moved in response to the operation of the operation member can be selected. Accordingly, the elongated member can be put into various curving motions.

In one aspect, the third guide groove is configured so as to guide the curving motion restricting member by the second region after guiding the curving motion restricting member by the first region when the operation member is operated starting from a state where the elongated member is in a rectilinear form.

In one aspect, the curving motion restricting member is guided by the second region after being guided by the first region. Therefore, the degree of restriction on the curving motion of the elongated member by the curving motion restricting member can be made to be different before and after the guiding of the curving motion restricting member in the second region.

In one aspect, the curving motion restricting member includes: a restriction member which is configured to be movable in the axial direction of the elongated member and which restricts the curving motion of the elongated member; and a connection member which is configured to be movable in the axial direction of the elongated member and which is connected to the restriction member. In one aspect, the connection member is so configured that its connection with the restriction member can be canceled, and the third guide groove guides a movement of the restriction member by way of the connection member.

In one aspect, the restriction member is guided by way of the connection member whose connection with the restriction member can be canceled. This makes it possible to move the restriction member in conjunction with the operation of the operation member when the restriction member and the connection member are connected, and to keep the restriction member unmoved when its connection with the connection member is canceled. Therefore, whether or not the restriction member is moved in conjunction with the operation of the operation member can be selected. Consequently, the elongated member can be made to perform a variety of curving motions.

In one aspect, a configuration may be adopted wherein the third guide groove is provided in one of the operation member and the connection member, the other of the operation member and the connection member is provided with a guide projection guided by the third guide groove, one of the restriction member and the connection member is provided with a groove portion for canceling the connection between the restriction member and the connection member, the other of the restriction member and the connection member is provided with an engaging projection for engagement with the groove portion, and the groove portion includes an axial groove provided in the axial direction of the elongated member, and an orthogonal groove orthogonal to the axial groove, such that the restriction member is connected to the connection member when the engaging projection engages the orthogonal groove, and that the connection between the restriction member and the connection member is canceled when the engaging projection engages the axial groove.

In one aspect, connection of the restriction member and the connection member to each other and canceling of the connection can be effected by means of the groove portion provided in one of the restriction member and the connection member. Therefore, the connection state between the restriction member and the connection member can be changed by a simple configuration.

In one aspect, the actuating member further includes a switching member that is provided to be rotatable in a circumferential direction of the elongated member, and that is configured to provide or cancel the connection of the restriction member and the connection member to each other according to a rotating direction thereof.

This configuration ensures that the connection state between the restriction member and the connection member can be switched by rotating the switching member. Therefore, the connection state can be switched easily.

In one aspect, the switching member is so configured as to fix the restriction member at a predetermined position in the axial direction of the elongated member when the switching member is switched to cancel the connection between the restriction member and the connection member.

According to this configuration, it is possible to prevent the restriction member from moving in the axial direction of the elongated member in a state where the connection between the restriction member and the connection member is canceled. Therefore, the elongated member can be prevented from performing a curving motion that is not intended.

In one aspect, the operation member is provided to be rotatable about an axis extending in a direction intersecting the axial direction of the elongated member, and configured such that rotation of the operation member causes the first moving part, the second moving part, and the curving motion restricting member to be moved.

This configuration ensures that the first moving part, the second moving part, and the curving motion restricting member can be moved by rotating the operation member. Consequently, operability of the actuating member can be enhanced.

According to one embodiment a medical instrument includes the actuating member according to the aforementioned embodiment of the invention, and the elongated member as aforementioned.

This makes it possible to obtain a medical instrument that can exhibit the aforementioned effects of the actuating member.

In addition, because it is unnecessary to wind the push-pull member around the operation member, a reduction in the overall size of the medical instrument can be realized.

Furthermore, the curving motions of the elongated member are effected by pushing/pulling of the push-pull member in the axial direction of the elongated member without changing the moving direction of the push-pull member. Therefore, pushing/pulling of the push-pull member can be efficiently transmitted to the elongated member.

DETAILED DESCRIPTION

Some embodiments of the present invention will be described below, based on the accompanying drawings.

Note that in the following description, a side with respect to a medical instrument on which the medical instrument is inserted into a living body of a patient, namely, the side of a distal end in an axial direction of an insertion portion of the medical instrument will be referred to as "the distal side," and a side on which the medical instrument is operated by hand, namely, the side of a proximal end in the axial direction of the insertion portion will be referred to as "the proximal side."

In addition, in a second embodiment and thereafter, component members having the same or similar functions to the functions of component members described in a first embodiment will be denoted by the same reference numerals as used for the component members in the first embodiment, and their descriptions will be omitted or simplified.

First Embodiment

Figure 1:
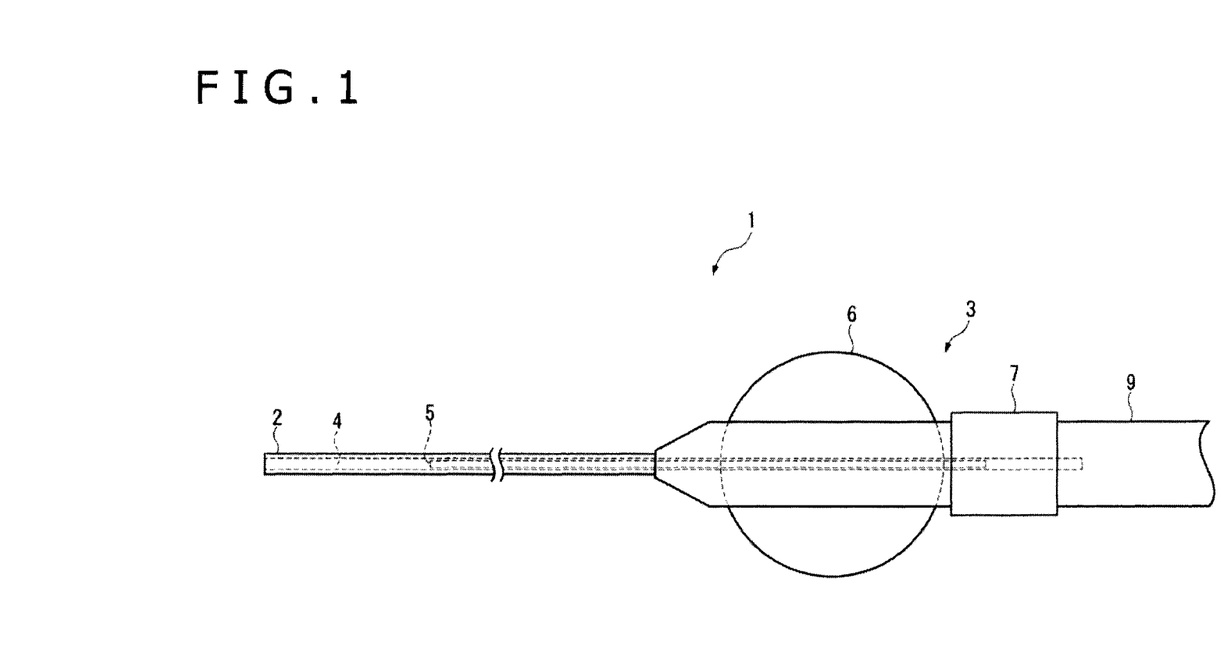
FIG. 1 is a schematic configuration view of a medical instrument according to a first embodiment of the present invention.

In FIG. 1, a medical instrument 1 includes: an insertion tube 2 provided as a flexible elongated member for medical use; and an actuating member 3 for causing the insertion tube 2 to perform a predetermined curving motion.

Figure 2:
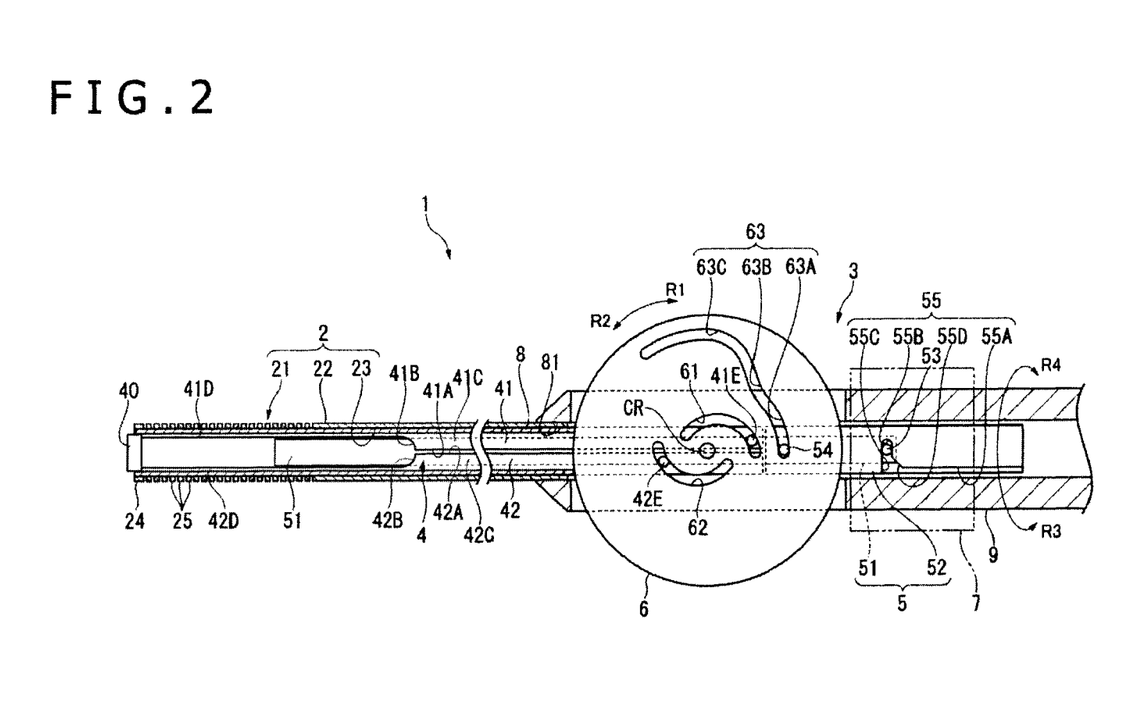
FIG. 2 is a side sectional view of the medical instrument of FIG. 1.

In FIG. 2, the insertion tube 2 includes: a flexible tube 21 configured to be curvable; a rigid tube 22 which is connected to the flexible tube 21 at its distal end and is supported by a grasping unit 9 at its proximal end; and a lumen 23 which is a continuous space inside the flexible tube 21 and the rigid tube 22 which has an opening at the distal end of the flexible tube 21.

The flexible tube 21 has a junction structure which includes a plurality of tubular bodies 24 and 25 and in which the plurality of tubular bodies 24 and 25 and the rigid tube 22 are linked in the axial direction in a mutually rotatable manner. The flexible tube 21 should have a very small outside diameter on the order of several millimeters, for enabling insertion thereof into a living body. On the other hand, an inside diameter of the flexible tube 21 is desirably set as large as possible, because the actuating member 3 and an article to be inserted such as a guide wire are inserted into or passed through the inside of the flexible tube 21. Therefore, the outside diameter of the flexible tube 21 is set in the range of about 0.5 to 20 mm (desirably 0.8 to 5 mm), the inside diameter is set in the range of about 0.4 to 18 mm (desirably 0.5 to 4.4 mm), and a material thickness is set in the range of about 0.1 to 2 mm (desirably 0.25 to 0.5 mm). In addition, at the time of curving, the radius of curvature is in the range of about 1 to 20 mm (desirably 5 to 10 mm), and a curvable angle range is 0 to 270 degrees (desirably 0 to 135 degrees). A length of the insertion tube 2 from the grasping unit 9 is set in the range of about 50 to 500 mm (desirably to 100 to 200 mm).

Such an insertion tube 2 as above is obtained, for example, by subjecting a stainless steel-made cylindrical tube-shaped member to laser beam machining. Where laser beam machining is applied, it is possible, by only cutting the cylindrical tube-shaped member by a laser beam, to easily obtain the insertion tube 2 in the state in which the rigid tube 22 and the tubular bodies 24 and 25 are mutually linked. Note that the material and production method for the insertion tube 2 are not limited to the aforesaid material and method, and other materials and methods can be used.

The actuating member 3 includes: a push-pull member 4 having a first moving part 41 and a second moving part 42 which are provided to be relatively movable in an axial direction of the insertion tube 2 and which are pushed and pulled in the axial direction of the insertion tube 2 so as to cause the insertion tube 2 to perform a curving motion; a curving motion restricting member 5 which is provided to be movable in the axial direction of the insertion tube 2 and which restricts the curving motion of the insertion tube 2; an operation member 6 for operating movements of the first moving part 41, the second moving part 42, and the curving motion restricting member 5; a switching member 7 which is provided to be rotatable in a circumferential direction of the insertion tube 2 and which switches the movement of the curving motion restricting member 5 relative to the operation member 6 according to the rotating direction; a seal part 8 which is provided at an outer circumference of the push-pull member 4 and which seals the push-pull member 4; and the grasping unit 9 which supports the push-pull member 4, the curving motion restricting member 5, the operation member 6, and the switching member 7 and which is grasped by an operator when performing a procedure.

Figure 3:
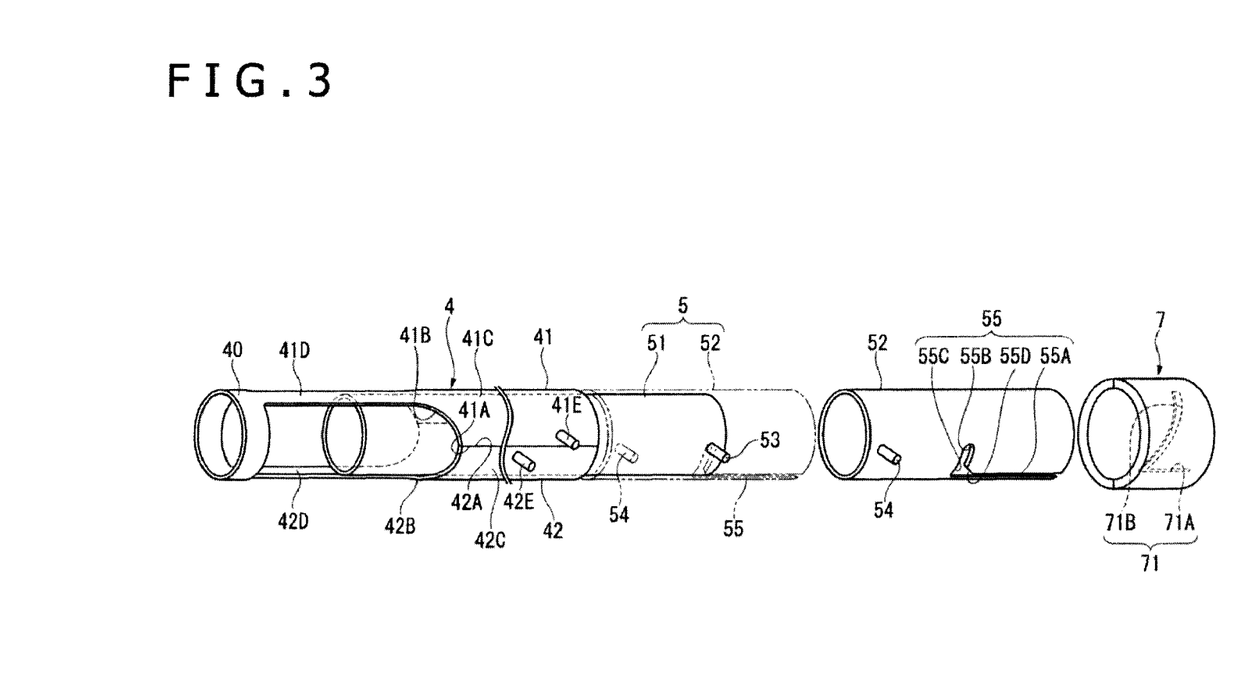
FIG. 3 is a perspective view of a push-pull member, a curving motion restricting member, and a switching member of the medical instrument shown in FIG. 1.

As shown in FIG. 3 also, the push-pull member 4 includes a tubular part 40, as well as the first moving part 41 and the second moving part 42 which extend proximally from the tubular part 40 and are provided to be relatively movable in the axial direction of the insertion tube 2. The push-pull member 4 is so configured that the first moving part 41 and the second moving part 42 are pushed and pulled in the axial direction of the insertion tube 2, whereby the flexible tube 21 is made to perform a curving motion.

The tubular part 40 is fixed to the insertion tube 2 in the state of protruding from the distal end of the insertion tube 2. By the tubular part 40, a distal portion of the insertion tube 2 is reduced in diameter.

The first moving part 41 and the second moving part 42 form a tubular structure, while being divided in the circumferential direction, inside the insertion tube 2.

The first moving part 41 includes: a cutout portion 41B where end edges 41A in a circumferential direction of the first moving part 41 are cut out; a large-width portion 41C which is a portion where the cutout portion 41B is not provided and which is shaped in such a manner that a cylindrical member is divided in the circumferential direction; a small-width portion 41D which is a portion where the cutout portion 41B is provided and which is smaller in width than the large-width portion 41C due to the presence of the cutout portion 41B; and a first projection 41E provided on the large-width portion 41C and projecting in a direction orthogonal to the end edge 41A.

The cutout portion 41B is formed by a method in which the end edges 41 on both sides in the circumferential direction are cut out at the same position in the axial direction and in the same shape. Note that in this embodiment, the cutout portion 41B is formed in an area between the tubular part 40 and the large-width portion 41C.

The large-width portion 41C is formed in a shape obtained by equally bisecting a cylindrical member in the circumferential direction. The end edges 41A in the circumferential direction of the large-width portion 41C are formed in a straight line shape, and are each in sliding contact along the axial direction with the end edge 42A of the second moving part 42 adjacent thereto. In other words, the first moving part 41 and the second moving part 42 are so formed that their end edges 41A and 42A in the circumferential direction, exclusive of the cutout portions 41B and 42B, make sliding contact with each other along the axial direction.

The small-width portion 41D extends in the axial direction at a substantially central position in the circumferential direction of the first moving part 41, and is so formed that its size in the circumferential direction is constant along the axial direction.

The first projection 41E is provided on the proximal side of a center-of-rotation CR of the operation member 6 (on the proximal side of the second projection 42E) in a state in which the flexible tube 21 is not curved.

The second moving part 42 is configured in the same fashion as the first moving part 41, except that the second projection 42E is provided in place of the first projection 41E, and can be described by replacing numeral 41 in the description of the first moving part 41 with numeral 42. In view of this, descriptions of other portions than the second projection 42E will be omitted.

The second projection 42E projects in a direction which is orthogonal to the end edge 42A and which is the same as the projecting direction of the first projection 41E of the first moving part 41. The second projection 42E is provided on the distal side of the center-of-rotation CR of the operation member 6 (on the distal side of the first projection 41E) in a state in which the flexible tube 21 is not curved.

As shown in FIG. 3 also, the curving motion restricting member 5 includes: a restriction member 51 which is provided to be movable in the axial direction of the insertion tube 2 and which restricts the curving motion of the insertion tube 2; and a connection member 52 which is provided to be movable in the axial direction of the insertion tube 2 and which is connected to the restriction member 51 in such a manner that its connection with the restriction member 51 can be canceled.

The restriction member 51 has a projection 53 as an engaging projection provided on the proximal side, and its portion on the distal side of the projection 53 can be advanced into and retracted from the inside of the push-pull member 4. The restriction member 51 is formed, for example, from a metal such as stainless steel, a nickel-titanium alloy, aluminum, etc. or a resin such as polyimide, polyamide, other plastics, etc., and is so configured as not to be curved even when the first moving part 41 and the second moving part 42 of the push-pull member 4 are put into a relative movement. In addition, the restriction member 51 is located in such a position that its distal portion overlaps the small-width portions 41D and 42D of the push-pull member 4 in a state in which a curving operation of the insertion tube 2 is not being effected by the operation member 6.

The connection member 52 includes a projection 54 as a guide projection provided on the distal side, and a groove portion 55 for canceling the connection of the connection member 52 with the restriction member 51. The groove portion 55 includes: an axial groove 55A provided along the axial direction of the insertion tube 2; a circumferential groove 55B provided along the circumferential direction of the insertion tube 2, as an orthogonal groove orthogonal to the axial groove 55A; and a connection groove 55C which connects the axial groove 55A and the circumferential groove 55B. The connection groove 55C is provided with a slant edge 55D at which an inside portion interposed between the axial groove 55A and the circumferential groove 55B is retracted (recessed) and which is inclined relative to both the axial groove 55A and the circumferential groove 55B. When the projection 53 engages the circumferential groove 55B, the restriction member 51 is connected to the connection member 52; on the other hand, when the projection 53 engages the axial groove 55A, the connection between the restriction member 51 and the connection member 52 is canceled.

The operation member 6 is composed of a disk-shaped member. The disk-shaped member includes, in its disk surface: a first guide groove 61 for engagement with the first projection 41E of the first moving part 41; a second guide groove 62 for engagement with the second projection 42E of the second moving part 42; and a third guide groove 63 for engagement with the projection 54 of the connection member 52. An outer circumferential surface of the disk-shaped member is rugged (minutely projected and recessed), though not shown. The operation member 6 is provided to be rotatable about the center-of-rotation CR, which is constituted of an axis extending in a direction orthogonal to the axial direction of the insertion tube 2. The movement of the first moving part 41 and the second moving part 42 is operable by rotating the operation member 6.

The first guide groove 61 and the second guide groove 62 are each formed in the shape of an arc of a true circle, and they are provided on opposite sides of the center-of-rotation CR of the operation member 6, with the inner sides of the circular arcs of them being oriented toward the center-of-rotation CR.

The first guide groove 61 is provided in such a position that the center of curvature thereof is spaced from the center-of-rotation CR toward the side of an end portion in a direction R1 of the first guide groove 61. In addition, the first guide groove 61 is so shaped that its end portion in the direction R1 is closer to the center-of-rotation CR than its end portion in a direction R2, and that its distance from the center-of-rotation CR gradually increases along the direction R1. In other words, the first guide groove 61 is so formed that a rotation of the operation member 6 in the direction R1 moves the first moving part 41 distally, whereas a rotation of the operation member 6 in the direction R2 moves the first moving part 41 proximally.

The second guide groove 62 is provided in such a position that the center of curvature thereof is spaced from the center-of-rotation CR toward the side of an end portion in the direction R1 of the second guide groove 62 (toward the side opposite to the center of curvature of the first guide groove 61). The second guide groove 62 is so shaped that its end portion in the direction R2 is closer to the center-of-rotation CR than its end portion in the direction R1, and that its distance from the center-of-rotation CR gradually increases along the direction R1. In other words, the second guide groove 62 is so formed that a rotation of the operation member 6 in the direction R1 moves the second moving part 42 proximally, whereas a rotation of the operation member 6 in the direction R2 moves the second moving part 42 distally.

The third guide groove 63 includes: a first region 63A so configured that the curving motion restricting member 5 is immovable; a second region 63B so configured that the curving motion restricting member 5 is movable; and a third region 63C connected to the second region 63B on the side opposite to the first region 63A and so configured that the curving motion restricting member 5 is immovable.

The first region 63A is formed in the shape of an arc of a true circle centered at the center-of-rotation CR, and is provided on the outer side of the first guide groove 61 in relation to the center-of-rotation CR.

The second region 63B is connected to the first region 63A and the third region 63C, and is so configured that its distance from the center-of-rotation CR increases along a direction toward the third region 63C.

The third region 63C is formed in the shape of an arc of a true circle which is centered at the center-of-rotation CR and which is greater in radius than the true circle pertaining to the first region 63A.

The third guide groove 63 as above is so configured as to further guide the curving motion restricting member 5 by the third region 63C, after the curving motion restricting member 5 is guided by the first region 63A and then the second region 63B, at the time when the operation member 6 is rotated starting from a state in which the flexible tube 21 is in a rectilinear form. In this instance, the third guide groove 63 guides a movement of the restriction member 51 by way of the connection member 52.

As shown in FIG. 3, the switching member 7 is composed of a tubular member that is formed with a groove portion 71 in an inner circumferential surface for engagement with the projection 53 of the curving motion restricting member 5. The switching member 7 is so configured as to fix the restriction member 51 at a predetermined position in the axial direction of the insertion tube 2, upon a switching such as to cancel the connection between the restriction member 51 and the connection member 52.

The groove portion 71 includes: an axial groove 71A provided along the axial direction of the insertion tube 2; and a spiral groove 71B which is connected to a distal portion of the axial groove 71A and which is formed to extend spirally from the distal portion.

The seal part 8 is fixed in close contact with the outer circumference of the push-pull member 4. The method for fixation here is not specifically limited; for example, adhesion with an adhesive, soldering (brazing), welding or the like may be used for the fixation. The material constituting the seal part 8 is, for example, a highly biocompatible resin such as fluororesins such as ethylene-tetrafluoroethylene copolymer (ETFE), polytetrafluoroethylene (PTFE), etc., polyolefins such as polyethylene (PE), polypropylene (PP), etc., and thermoplastic resins such as polyamide, polyester, polyurethane, etc. Note that the seal part 8 may be disposed on the inner side of the push-pull member 4 or on the outer side of the insertion tube 2.

The grasping unit 9 is formed, for example, from a rigid resin material, and supports the insertion tube 2, the push-pull member 4, the curving motion restricting member 5, the operation member 6, and the switching member 7. The grasping unit 9 is provided with a through-hole 91 through which a treatment instrument such as an endoscope is to be passed. The insertion tube 2 is supported by the grasping unit 9, with a proximal portion of the insertion tube 2 inserted in the through-hole 91.

A curving motion of the insertion tube 2 effected by the actuating member 3 will be described below.

Figure 4:
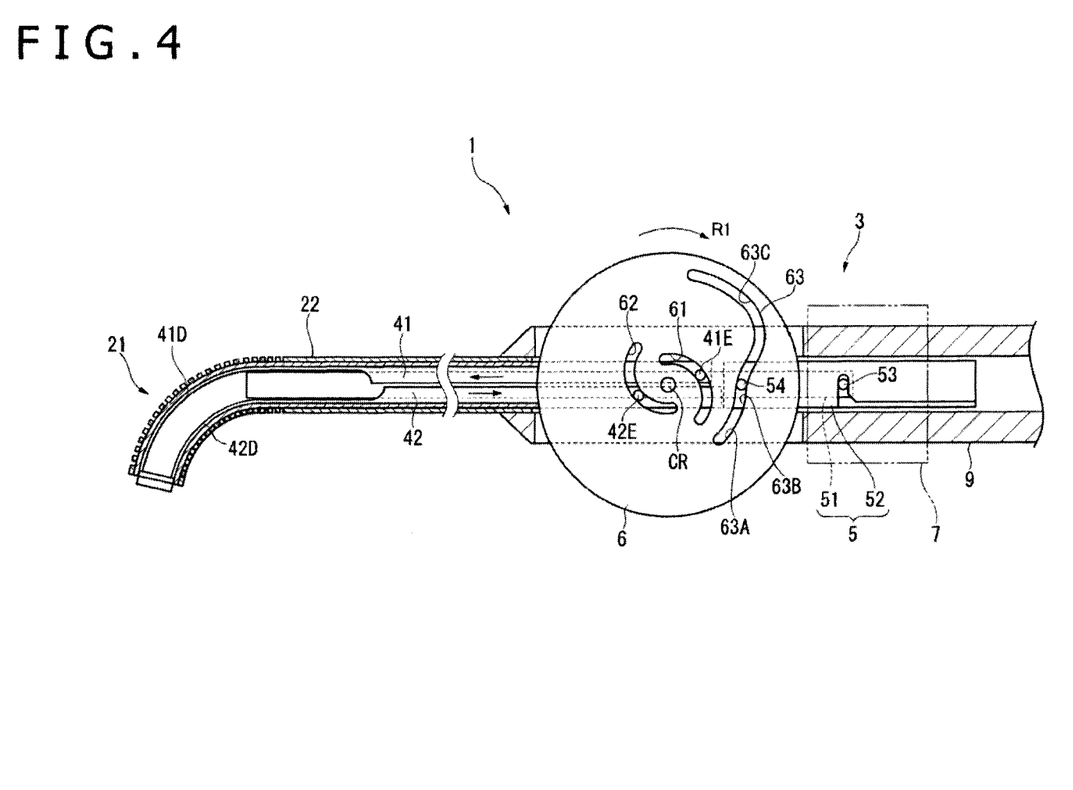
FIG. 4 illustrates an operation of the medical instrument shown in FIG. 1.

When the operation member 6 is rotated in the direction R1 starting from a state where the insertion tube 2 is in a rectilinear form, the first projection 41E is guided by the first guide groove 61, whereby the first moving part 41 is moved distally, as shown in FIG. 4. Concurrently, the second projection 42E is guided by the second guide groove 62, whereby the second moving part 42 is moved proximally. As a result, the two small-width portions 41D and 42D, opposed to each other, of the push-pull member 4 are curved in a plane passing these small-width portions 41D and 42D, so that the flexible tube 21 is curved (bent) downward.

Figure 5A:
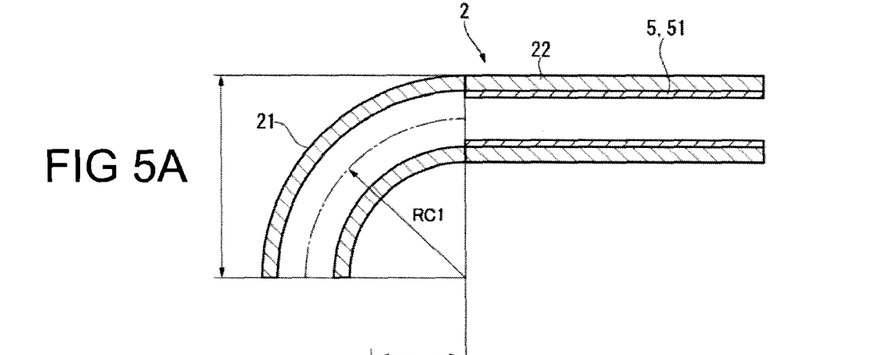
FIG. 5A shows a schematic view illustrating an operation of the curving motion restricting member of the medical instrument shown in FIG. 1 with the curving motion restricting member in a proximal position.
Figure 5B:
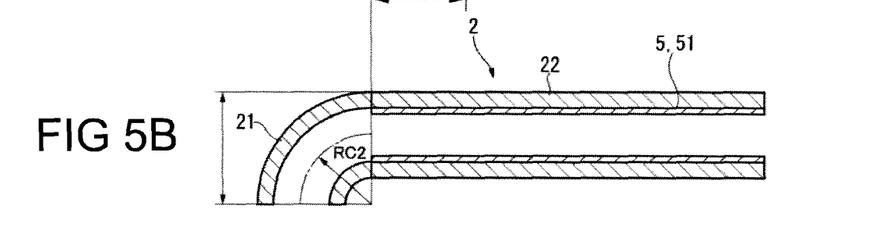
FIG. 5B shows a schematic view illustrating an operation of the curving motion restricting member of the medical instrument shown in FIG. 1 with the curving motion restricting member in a distal position.

In this instance, the projection 54 is in engagement with the first region 63A of the third guide groove 63. Because the first region 63A is formed in the shape of an arc of a true circle centered at the center-of-rotation CR, the projection 54 is not moved, and the connection member 52 is not moved, either. Therefore, the restriction member 51 remains in such a position that its distal portion overlaps the small-width portions 41D and 42D of the push-pull member 4, so that the small-width portions 41D and 42D of the push-pull member 4 and a proximal side of the flexible tube 21 are restricted by the distal portion of the restriction member 51 from curving. This ensures that only a distal portion of the flexible tube 21 curves (bends). As shown in FIGS. 5A and 5B, therefore, a radius-of-curvature RC2 of the flexible tube 21 that is accompanied by the curving motion restricting member 5 (as shown in FIG. 5B) can be made smaller, as compared with a radius-of-curvature RC1 of the flexible tube 21 that is not accompanied by the curving motion restricting member 5 (as shown in FIG. 5A). Accordingly, the insertion tube 2 can be curved with a small radius-of-curvature RC2, from a stage where the operation amount of the operation member 6 is small.

When the operation member 6 is rotated further in the direction R1, the projection 54 is guided by the second region 63B of the third guide groove 63. Therefore, the connection member 52 is gradually moved proximally, and the restriction member 51 is also moved proximally by way of the connection member 52. This causes the flexible tube 21 to curve from a more proximal side. Accordingly, further curving of the flexible tube 21 is enabled.

Figure 6:
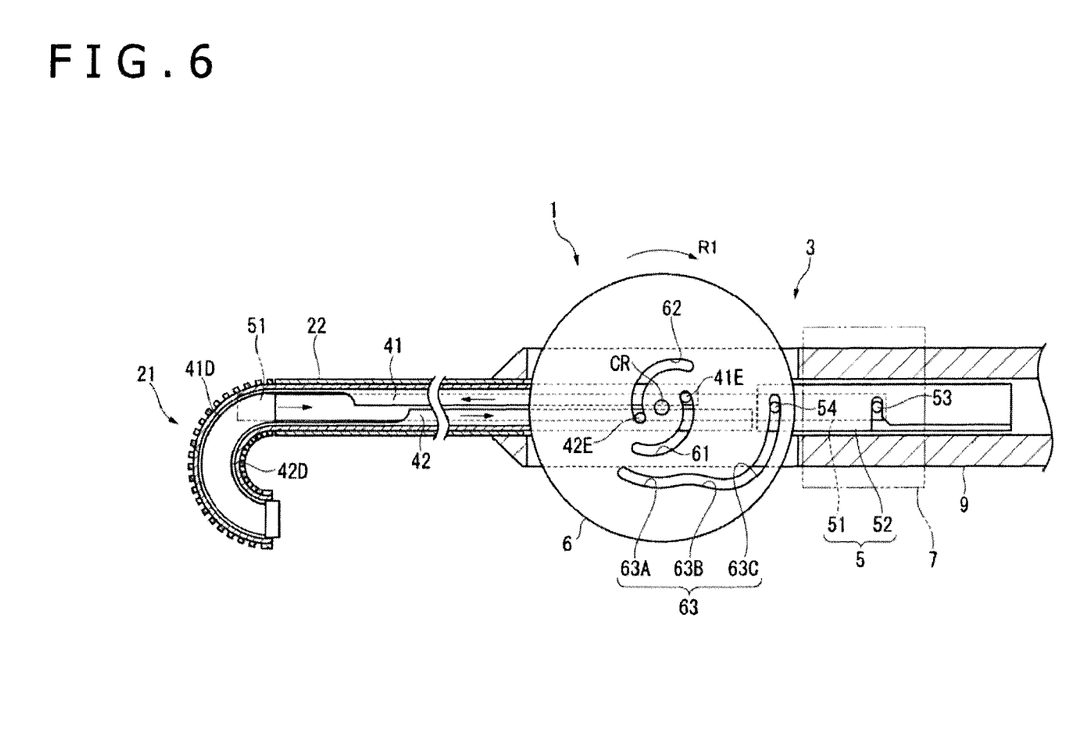
FIG. 6 illustrates an operation of the medical instrument shown in FIG. 1.

When the operation member 6 is rotated further in the direction R1, as shown in FIG. 6, the distal portion of the restriction member 51 is accommodated in the rigid tube 22, and the projection 54 is guided by the third region 63C of the third guide groove 63. Because the third region 63C is formed in the shape of an arc of a true circle centered at the center-of-rotation CR, the connection member 52 is not moved any more, and the restriction member 51 is stopped. Thereafter, the restriction by the restriction member 51 is removed. Therefore, the flexible tube 22 becomes curvable from its portion of connection with the rigid tube 22, and performs a curving motion which is the same as that in the case where the curving motion restricting member 5 is not provided.

In the case of canceling the connection between the restriction member 51 and the connection member 52 by the switching member 7, the switching member 7 is rotated in a direction R3 as shown in FIG. 2. This causes the projection 53 of the restriction member 51 to be pressed downward by the spiral groove 71B and rotates the restriction member 51 in the direction R3, starting from a state where the projection 53 is in engagement with the circumferential groove 55B of the connection member 52 as shown at the leftmost position in FIG. 7. Consequently, as shown on the upper side at the second position from the left in FIG. 7, the projection 53 is moved along the slant edge 55D within the connection groove 55C of the connection member 52.

Figure 7:
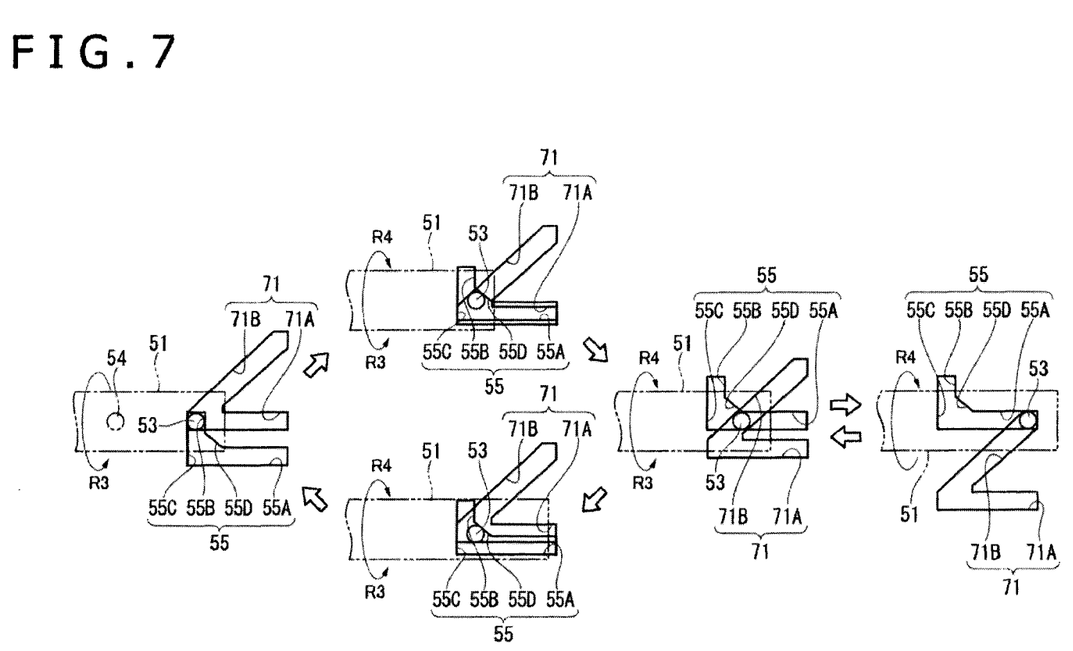
FIG. 7 shows schematic views illustrating an operation of the switching member of the medical instrument shown FIG. 1.

When the switching member 7 is rotated further in the direction R3, as shown at the third position from the left in FIG. 7, the projection 53 is guided by the spiral groove 71B of the switching member 7 and the slant edge 55D of the connection member 52, to be moved into the axial groove 55A of the connection member 52. As a result, the connection between the restriction member 51 and the connection member 52 is canceled, and the restriction member 51 is freed from interlocking with the operation of the operation member 6. When the switching member 7 is rotated further in the direction R3, as shown at the rightmost position in FIG. 7, the projection 53 is moved proximally within the axial groove 55A. Then, the projection 53 is locked in the axial groove 55A of the connection member 52 by a deepest end portion of the spiral groove 71B of the switching member 7. As a result, the restriction member 51 is fixed at a predetermined position in the axial direction of the insertion tube 2, specifically, at such a position that the distal end of the restriction member 51 is accommodated in the rigid tube 22.

On the other hand, in the case of connecting the restriction member 51 and the connection member 52 by the switching member 7, the switching member 7 is rotated in a direction R4. As a result, as indicated by left arrows in FIG. 7, the restriction member 51 and the connection member 52 are connected to each other through a process reverse to the process of canceling the connection.

This embodiment, configured as described above, produces the following effects.

By operating the operation member 6, it is possible to move the first moving part 41, the second moving part 42, and the curving motion restricting member 5 by means of the guide grooves 61, 62, and 63. At the time of curving the insertion tube 2 by a relative movement of the first moving part 41 and the second moving part 42—the curving motion of the insertion tube 2 can be restricted according to the moved position of the curving motion restricting member 5. Therefore, the insertion tube 2 can be put into a variety of curving motions, according to the settings of the guide grooves 61, 62, and 63. Consequently, the insertion tube 2 can be appropriately curved according to a target site in a living body.

The curving motion restricting member 5 can be set to move or not to move in response to an operation of the operation member 6. Accordingly, the insertion tube 2 is enabled to perform a diversity of curving motions.

In addition, the curving motion restricting member 5 is guided by the second region 63B after being guided by the first region 63A. This ensures that the degree of restriction on the curving motion of the insertion tube 2 by the curving motion restricting member 5 can be made to be different before and after the guiding of the curving motion restricting member 5 by the second region 63B.

The restriction member 51 is guided by way of the connection member 52 whose connection with the restriction member 51 can be canceled. This ensures that the restriction member 51 can be moved in conjunction with the operation of the operation member 6 when the restriction member 51 and the connection member 52 are connected, and that the restriction member 51 can be kept unmoved when the connection thereof with the connection member 52 is canceled. Therefore, whether or not the restriction member 51 is moved in conjunction with the operation of the operation member 6 can be selected. Consequently, the insertion tube 2 is enabled to perform a plurality of curving motions.

Further, connection between the restriction member 51 and the connection member 52 and canceling of the connection can be effected by means of the groove portion 55 provided in the connection member 52. Therefore, the connection state between the restriction member 51 and the connection member 52 can be changed by a simple configuration.

In addition, because the connection state between the restriction member 51 and the connection member 52 can be switched by rotating the switching member 7, the connection state can be switched easily.

The restriction member 51 can be prevented from moving in the axial direction of the insertion tube 2, in a state where the connection between the restriction member 51 and the connection member 52 is canceled. This makes it possible to prevent the insertion tube 2 from performing a curving motion that is not intended.

Further, because the first moving part 41, the second moving part 42, and the curving motion restricting member 5 can be moved by rotating the operation member 6, operability of the actuating member 3 can be enhanced.

In addition, since it is unnecessary to wind the push-pull member 4 around the operation member 6, a reduction in the overall size of the medical instrument 1 can be realized.

Furthermore, curving motions of the insertion tube 2 are effected by pushing/pulling of the push-pull member 4 in the axial direction of the insertion tube 2 without changing the operating direction of the push-pull member 4. This enables the pushing/pulling of the push-pull member 4 to be efficiently transmitted to the insertion tube 2.

Second Embodiment

Figure 8:
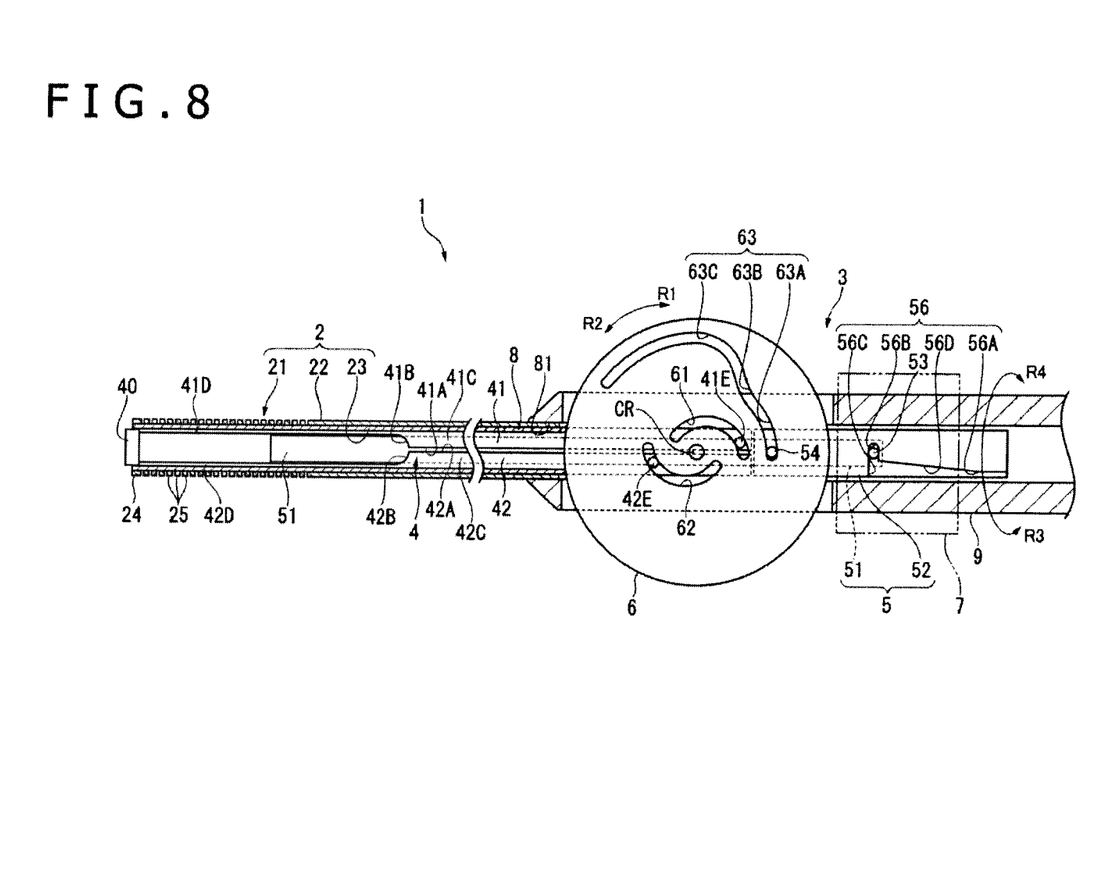
FIG. 8 is a side sectional view of a medical instrument according to a second embodiment of the present invention.
Figure 9:
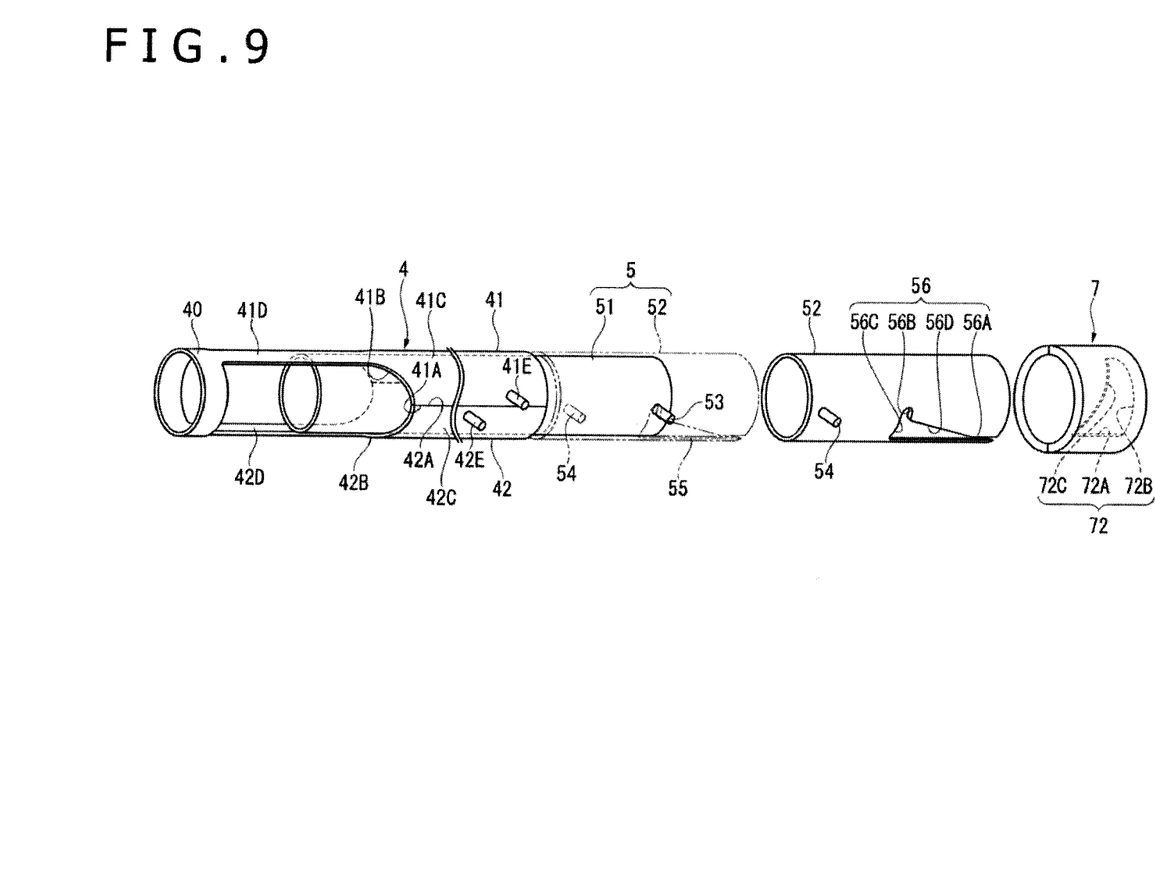
FIG. 9 is a perspective view of a push-pull member, a curving motion restricting member, and a switching member of the medical instrument shown in FIG. 8.

A medical instrument 1 according to a second embodiment of the present invention, as shown in FIGS. 8 and 9, differs from the first embodiment in a configuration of a groove portion 56 of a connection member 52 and in a configuration of a groove portion 72 of a switching member 7.

The groove portion 56 includes an axial groove 56A, a circumferential groove 56B, and a connection groove 56C. The axial groove 56A and the circumferential groove 56B are formed to be smaller than the connection groove 56C. The connection groove 56C has a slant edge 56D retracted (recessed) more, as compared with that in the first embodiment; thus, in a development of the connection member 52, the shape of the connection groove 52 is more like a triangle, as compared with that in the first embodiment.

The groove portion 72 includes: an axial edge 72A along the axial direction of the insertion tube 2; a circumferential edge 72B which is orthogonal to the axial edge 72A and is provided in the circumferential direction of the insertion tube 2; and a slant edge 72C facing the axial edge 72A and the circumferential edge 72B. In a development of the switching member 7, the groove portion 72 is generally triangular in shape.

In the medical instrument 1 according to a second embodiment as described above, at the time of canceling the connection between the restriction member 51 and the connection member 52 by the switching member 7, the switching member 7 is rotated in a direction R3 as shown in FIG. 8. This causes the projection 53 of the restriction member 51 to be pressed downward by the slant edge 72C and rotates the restriction member 51 in the direction R3, from a state where the projection 53 is in engagement with the circumferential groove 56B as shown at the leftmost position in FIG. 10. Consequently, as shown on the upper side at the second position from the left in FIG. 10, the projection 53 is moved along the slant edge 56D within the connection groove 56C of the connection member 52.

Figure 10:
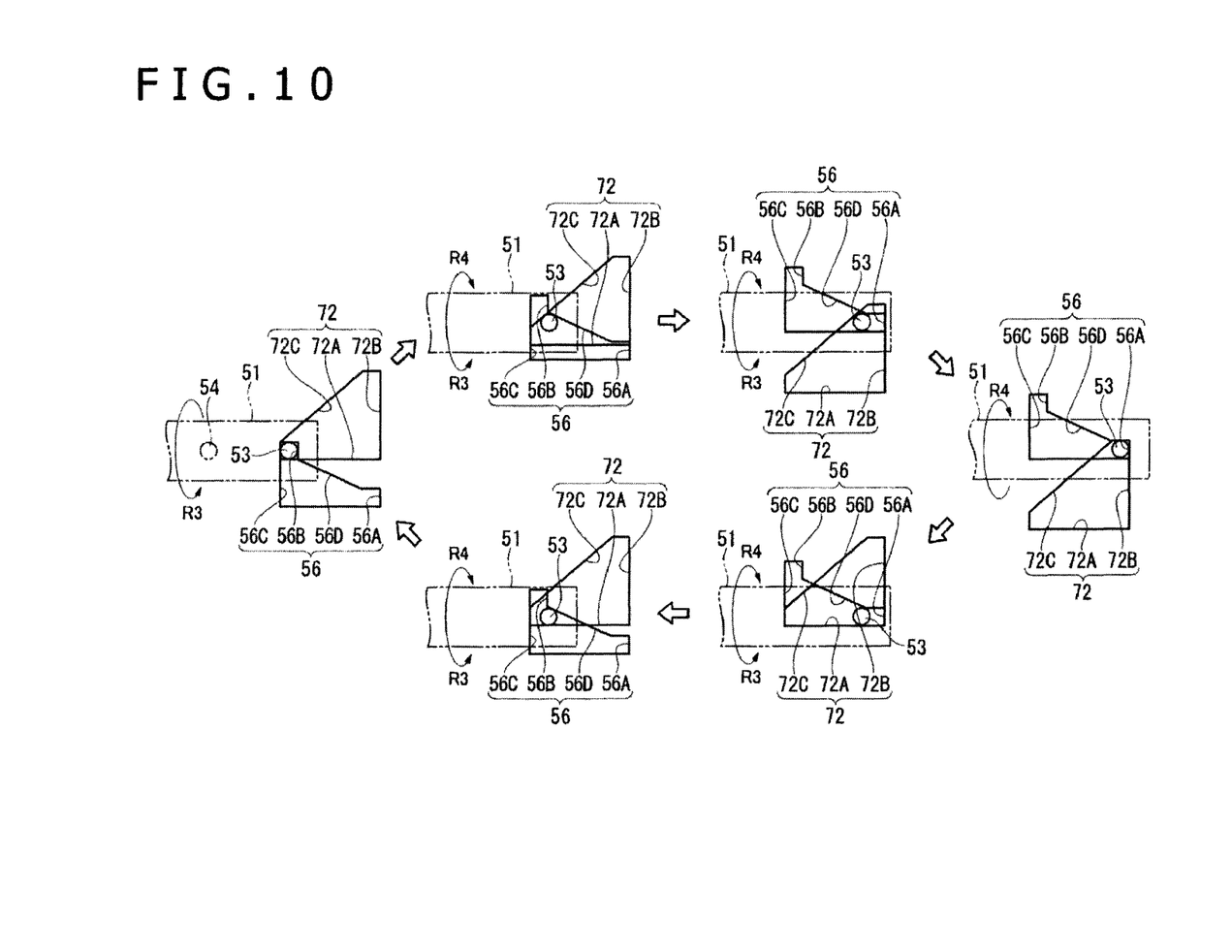
FIG. 10 shows schematic views illustrating an operation of the switching member of the medical instrument shown in FIG. 8.

When the switching member 7 is rotated further in the direction R3, as shown on the upper side at the third position from the left in FIG. 10, the projection 53 is guided by the slant edge 72C of the switching member 7 and the slant edge 56D of the connection member 52, to be moved into the axial groove 56A of the connection member 52. As a result, the connection between the restriction member 51 and the connection member 52 is canceled, and the restriction member 51 is freed from interlocking with the operation of the operation member 6. When the switching member 7 is rotated further in the direction R3, as shown at the rightmost position in FIG. 10, the projection 53 is moved proximally within the axial groove 56A. Then, the projection 53 is locked in the axial groove 56A of the connection member 52 by an end portion between the circumferential edge 72B and the slant edge 72C in the groove portion 72 of the switching member 7. As a result, the restriction member 51 is fixed at a predetermined position such that a distal portion thereof is accommodated in the rigid tube 22.

On the other hand, in the case of connecting the restriction member 51 and the connection member 52 by the switching member 7, the switching member 7 is rotated in the direction R4. As a result, as indicated by left arrows in FIG. 10, the restriction member 51 and the connection member 52 are connected to each other through a process reverse to the process of canceling the connection.

Note that the present invention is not limited to the aforementioned embodiments, and modifications, improvements and the like within such a scope that the object of the present invention can be achieved are included in the present invention.

As the insertion tube 2, an arbitrary tube can be used insofar as at least a part thereof is provided to be curvable; for example, the insertion tube 2 as a whole may be composed of the flexible tube 21. In addition, instead of using the flexible tube 21, a flexible tube 21 may be composed of a flexible blank material or materials, or the insertion tube as a whole may be composed of the flexible blank material or materials. In this case, the insertion tube 2 may not necessarily be cylindrical in shape but may be polygonal in cross-sectional shape.

The push-pull member 4 is not limited to the one in the above embodiments; for instance, the tubular part 40 may be formed in an annular shape. The tubular part 40 may be bisected in the circumferential direction, and the halves may be constituted as part of the first moving part 41 and the second moving part 42, respectively.

In addition, the push-pull member 4 may lack the tubular part 40. In this case, for example, distal portions in the axial direction of the first moving part 41 and the second moving part 42 may be connected to the flexible tube 21 of the insertion tube 2 or to the insertion tube 2 at a position distally of the flexible tube 21, whereby it is ensured that the insertion tube 2 can be curved.

Furthermore, it suffices for the push-pull member 4 to be so configured that a distal-side portion of the insertion tube 2 can be pushed and pulled through relative movements of the first moving part 41 and the second moving part 42. For instance, the push-pull member 4 may be a traction wire, a plate-shaped belt member or the like.

The curving motion restricting member 5 may be composed of the restriction member 51. In this case, with the projection 53 of the restriction member 51 put in engagement with the third guide groove 63 of the operation member 6, movement of the curving motion restricting member 5 can be guided by the third guide groove 63.

In addition, the curving motion restricting member 5 may be disposed on the outside of the push-pull member 4 or on the outside of the flexible tube 21.

Furthermore, the connection groove 55C and 56C of the connection member 52 may be formed in a curved line shape. In this case, the projection 53 of the restriction member 51 can be guided by the connection groove 55C and 56C more smoothly.

The operation member 6 may have any shape insofar as it enables the first moving part 41, the second moving part 42, and the curving motion restricting member 5 to be moved in the axial direction of the insertion tube 2.

For instance, the operation member 6 may be so configured that when the operation member 6 is rotated starting from a state where the insertion tube 2 is in a rectilinear form, the curving motion restricting member 5 is guided by the second region 63B and by the first region 63A after it is guided by the third region 63C. In this case, it can be ensured that restriction of a curving motion of the insertion tube 2 by the curving motion restricting member 5 is not performed at a stage where the operation amount of the operation member 6 is small, and that the restriction by the curving motion restricting member 5 is performed at a stage where the operation amount is in excess of a predetermined amount.

In addition, the operation member 6 may be so configured as to enable the first moving part 41 and the second moving part 42 to be moved respectively in opposite directions along the axial direction of the insertion tube 2.

Furthermore, the operation member 6 may be composed of a tubular member having a first guide groove, a second guide groove, and a third guide groove formed in an inner circumferential surface thereof, and may be so configured as to move the first moving part 41, the second moving part 42, and the curving motion restricting member 5 by rotating the operation member 6 in the circumferential direction of the insertion tube 2.

A configuration may be adopted wherein the operation member 6 is provided with a first projection and a second projection, the first moving part 41 is provided with a first guide groove, and the second moving part 42 is provided with a second guide groove. Furthermore, another configuration may be adopted wherein the first moving part 41 is provided with a first guide groove, the second moving part 42 is provided with a second projection, and the push-pull member 4 is provided with a first projection and a second guide groove; or, alternatively, a combination reverse to the combination of the above described configuration may be adopted.

In addition, the first guide groove 61 and the second guide groove 62 may not necessarily penetrate the operation member 6 but may be formed in a recessed form.

It should be understood by those skilled in the art that various modifications, combinations, sub-combinations and alterations may occur depending on design requirements and other factors insofar as they are within the scope of the appended claims or the equivalents thereof.

What is claimed is:

1. An actuating member for causing a flexible elongated member for medical use to perform a predetermined curving motion, the actuating member comprising:
    a push-pull member comprising a first moving part and a second moving part which are configured to be movable relative to one another in an axial direction of the elongated member, the first moving part and the second moving part being pushable and pullable so as to cause the elongated member to curve in the axial direction of the elongated member;
    a curving motion restricting member which is configured to be movable in the axial direction of the elongated member, and which is configured to restrict curving of at least a portion of the elongated member; and
    an operation member configured to operate movements of the first moving part, the second moving part, and the curving motion restricting member,
    wherein a surface of the operation member includes:
        a first guide groove configured to guide movement of the first moving part,
        a second guide groove configured to guide movement of the second moving part, and
        a third guide groove configured to guide movement of the curving motion restricting member.

2. The actuating member according to claim 1, wherein the third guide groove comprises a first region configured to allow the curving motion restricting member to be immovable, and a second region configured to allow the curving motion restricting member to be movable.

3. The actuating member according to claim 2, wherein the third guide groove is configured so as to guide the curving motion restricting member by the second region after guiding the curving motion restricting member by the first region when the operation member is operated starting from a state where the elongated member is in a rectilinear form.

4. The actuating member according to claim 1, wherein the curving motion restricting member comprises:

a restriction member which is configured to be movable in the axial direction of the elongated member and which is configured to restrict the curving motion of at least a portion of the elongated member; and a connection member which is configured to be movable in the axial direction of the elongated member and which is connectable to and disconnectable from the restriction member, wherein the third guide groove is configured to guide movement of the restriction member via the connection member.

5. The actuating member according to claim 4, wherein the connection member includes a guide projection configured to be guided by the third guide groove.

6. The actuating member according to claim 5, wherein one of the restriction member and the connection member includes a groove portion configured to allow for disconnection of the restriction member and the connection member, and the other of the restriction member and the connection member includes an engaging projection configured to engage with the groove portion.

7. The actuating member according to claim 6, wherein the groove portion includes an axial groove provided in the axial direction of the elongated member, and an orthogonal groove orthogonal to the axial groove, the axial groove and the orthogonal groove being configured such that the restriction member is connected to the connection member when the engaging projection engages the orthogonal groove, and such that the restriction member is disconnected from the connection member when the engaging projection engages the axial groove.

8. The actuating member according to claim 4, further comprising a switching member which is configured to be rotatable in a circumferential direction of the elongated member, and which is configured to switch between connection and disconnection of the restriction member and the connection member to each other.

9. The actuating member according to claim 8, wherein, upon switching to disconnect the connection between the restriction member and the connection member, the switching member is configured to fix the restriction member at a predetermined position in the axial direction of the elongated member.

10. The actuating member according to claim 1, wherein the operation member is configured to be rotatable about an axis extending in a direction intersecting the axial direction of the elongated member, and is configured such that rotation of the operation member causes the first moving part, the second moving part, and the curving motion restricting member to be moved.

11. The actuating member according to claim 1, wherein the push-pull member further comprises a tubular part from which the first moving part and the second moving part extend.

12. A medical instrument comprising:
an elongated member; and
an actuating member comprising:
a push-pull member comprising a first moving part and a second moving part which are configured to be movable relative to one another in an axial direction of the elongated member, the first moving part and the second moving part being pushable and pullable so as to cause the elongated member to curve in the axial direction of the elongated member;
a curving motion restricting member which is configured to be movable in the axial direction of the elongated member, and which is configured to restrict curving of at least a portion of the elongated member; and an operation member configured to operate movements of the first moving part, the second moving part, and the curving motion restricting member,
wherein a surface of the operation member includes:
a first guide groove configured to guide movement of the first moving part,
a second guide groove configured to guide movement of the second moving part, and
a third guide groove configured to guide movement of the curving motion restricting member.

13. The medical instrument according to claim 12, wherein the curving motion restricting member comprises:
a restriction member which is configured to be movable in the axial direction of the elongated member and which is configured to restrict the curving motion of at least a portion of the elongated member; and
a connection member which is configured to be movable in the axial direction of the elongated member and which is connectable to and disconnectable from the restriction member,
wherein the third guide groove is configured to guide movement of the restriction member via the connection member.

14. The actuating member according to claim 13, the connection member includes a guide projection configured to be guided by the third guide groove.

15. The actuating member according to claim 14, wherein one of the restriction member and the connection member includes a groove portion configured to allow for disconnection of the restriction member and the connection member, and the other of the restriction member and the connection member includes an engaging projection configured to engage with the groove portion.

16. The actuating member according to claim 15, wherein the groove portion includes an axial groove provided in the axial direction of the elongated member, and an orthogonal groove orthogonal to the axial groove, the axial groove and the orthogonal groove being configured such that the restriction member is connected to the connection member when the engaging projection engages the orthogonal groove, and such that the restriction member is disconnected from the connection member when the engaging projection engages the axial groove.

17. The actuating member according to claim 13, further comprising a switching member which is configured to be rotatable in a circumferential direction of the elongated member, and which is configured to switch between connection and disconnection of the restriction member and the connection member to each other.

18. The actuating member according to claim 17, wherein, upon switching to disconnect the connection between the restriction member and the connection member, the switching member is configured to fix the restriction member at a predetermined position in the axial direction of the elongated member.

19. An actuating member for causing a flexible elongated member for medical use to perform a predetermined curving motion, the actuating member comprising:
a push-pull member comprising a first moving part and a second moving part which are configured to be movable relative to one another in an axial direction of the elongated member, the first moving part and the second moving part being pushable and pullable so as to cause the elongated member to curve in the axial direction of the elongated member;

a curving motion restricting member which is configured to be movable in the axial direction of the elongated member, and which is configured to restrict curving of at least a portion of the elongated member; and an operation member configured to operate movements of the first moving part, the second moving part, and the curving motion restricting member, wherein one of the first moving part and the operation member includes a first guide groove configured to guide movement of the first moving part, wherein one of the second moving part and the operation member includes a second guide groove configured to guide movement of the second moving part, wherein one of the curving motion restricting member and the operation member includes a third guide groove configured to guide movement of the curving motion restricting member, wherein the third guide groove comprises a first region configured to allow the curving motion restricting member to be immovable, and a second region configured to allow the curving motion restricting member to be movable, and wherein the third guide groove is configured so as to guide the curving motion restricting member by the second region after guiding the curving motion restricting member by the first region when the operation member is operated starting from a state where the elongated member is in a rectilinear form.

20. An actuating member for causing a flexible elongated member for medical use to perform a predetermined curving motion, the actuating member comprising:

a push-pull member comprising a first moving part and a second moving part which are configured to be movable relative to one another in an axial direction of the elongated member, the first moving part and the second moving part being pushable and pullable so as to cause the elongated member to curve in the axial direction of the elongated member;

a curving motion restricting member which is configured to be movable in the axial direction of the elongated member, and which is configured to restrict curving of at least a portion of the elongated member; and an operation member configured to operate movements of the first moving part, the second moving part, and the curving motion restricting member, wherein one of the first moving part and the operation member includes a first guide groove configured to guide movement of the first moving part, wherein one of the second moving part and the operation member includes a second guide groove configured to guide movement of the second moving part, wherein one of the curving motion restricting member and the operation member includes a third guide groove configured to guide movement of the curving motion restricting member, wherein the curving motion restricting member comprises:
 a restriction member which is configured to be movable in the axial direction of the elongated member and which is configured to restrict the curving motion of at least a portion of the elongated member, and
 a connection member which is configured to be movable in the axial direction of the elongated member and which is connectable to and disconnectable from the restriction member, and wherein the third guide groove is configured to guide movement of the restriction member via the connection member.

* * * * *